US00PP30254P2

(12) United States Plant Patent
Van Dijk

(10) Patent No.: US PP30,254 P2
(45) Date of Patent: Feb. 26, 2019

(54) ***ANTHURIUM* PLANT NAMED 'ANTHEUDAM'**

(50) Latin Name: ***Anthurium andreanum* L.**
Varietal Denomination: ANTHEUDAM

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 24 days.

(21) Appl. No.: 15/732,058

(22) Filed: Sep. 11, 2017

(51) Int. Cl.
*A01H 5/02* (2018.01)

(52) U.S. Cl.
USPC ..... Plt./366
CPC ..... *A01H 5/02* (2013.01)

(58) Field of Classification Search
USPC ..... Plt./366
See application file for complete search history.

(56) References Cited

PUBLICATIONS

UPOV hit on *Anthurium* plant named 'Antheudam', QZ PBR 47032, filed Nov. 24, 2015.*

* cited by examiner

*Primary Examiner* — Anne Marie Grunberg
(74) *Attorney, Agent, or Firm* — Jondle & Associates, P.C.

(57) ABSTRACT

A new *Anthurium* plant named 'ANTHEUDAM' particularly distinguished by having large, shiny and strongly blistered, bright red, cordate and very durable spathes that retain the original color for a very long period of time, dark, elliptical cordate durable leaves, white spadix with yellow-orange tips, early and rich flowering continuously through the year, and a plant height of 45.0 cm to 50.0 cm is disclosed.

3 Drawing Sheets

Genus and species: *Anthurium andreanum* L.
Variety denomination: 'ANTHEUDAM'.

BACKGROUND OF THE NEW PLANT

The present invention comprises a new and distinct variety of *Anthurium*, botanically known as *Anthurium andreanum* L., and hereinafter referred to by the variety name 'ANTHEUDAM'. The new *Anthurium* plant is a product of a planned breeding program conducted by the inventor in Bleiswijk, the Netherlands. The objective of this breeding program was to create a new 45.0 cm to 50.0 cm height plant with large, shiny and strongly blistered, bright red, cordate and durable spathes.

The new variety originated from a cross-pollination made in November 2008 in Bleiswijk, The Netherlands. The female parent was a red *Anthurium* pot plant designated '10520-01' (unpatented), and the male parent was a red *Anthurium* pot plant designated '9863-01' (unpatented).

A single plant was selected from the progeny of the stated cross in September 2010 and has been asexually reproduced repeatedly by tissue culture in Bleiswijk, The Netherlands over a 7-year period. The present invention has been found to retain its distinctive characteristics through successive asexual propagations.

Plant Breeder's Rights for this variety have been applied for in the European Union on Nov. 24, 2015. 'ANTHEUDAM' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, The Netherlands:

1) Large, shiny, strongly blistered, bright red and cordate spathe;
2) White spadix with yellow-orange tip; and
3) Green, elliptical cordate leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 52-week old plant grown in a greenhouse in Bleiswijk, The Netherlands in June 2017. Colors in the photographs may differ from the color values cited in the detailed botanical description, which accurately describe the actual colors of the new variety.

DESCRIPTION OF THE NEW VARIETY

Figure 1:
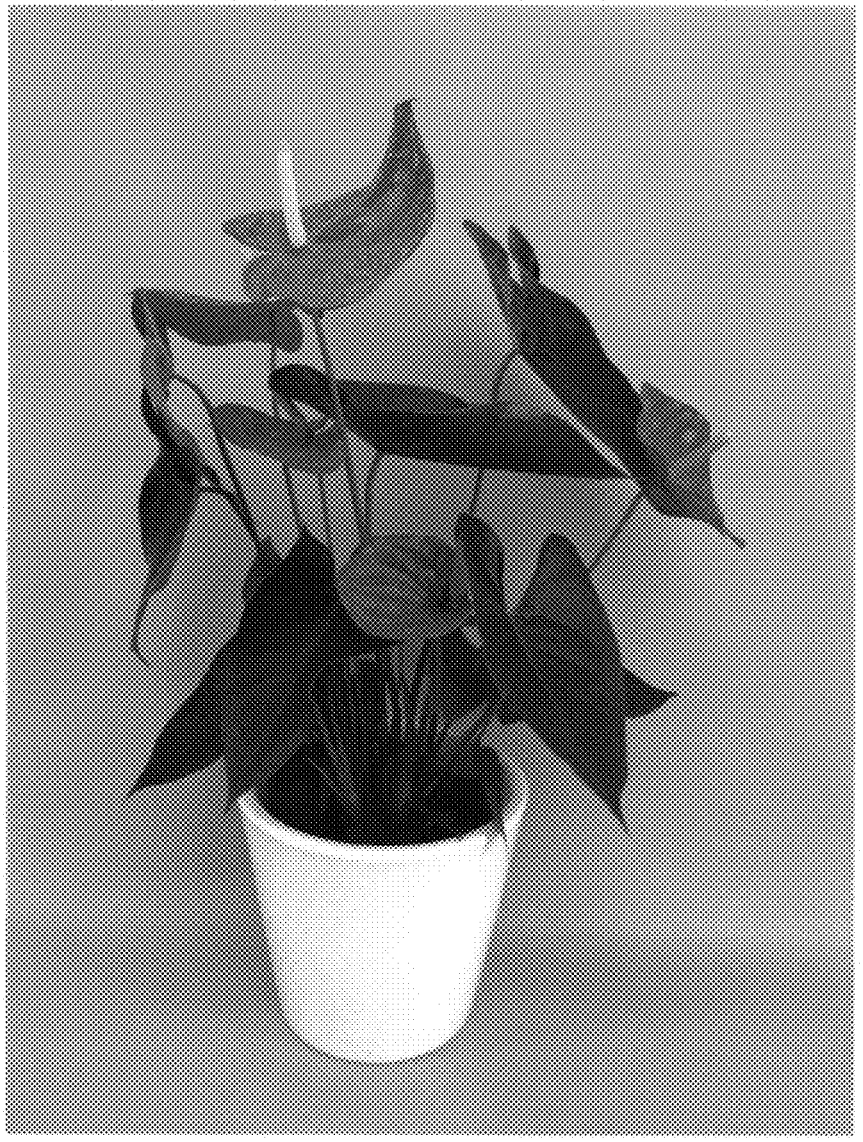
FIG. 1 shows the overall plant habit, including blooms and foliage.
Figure 2:
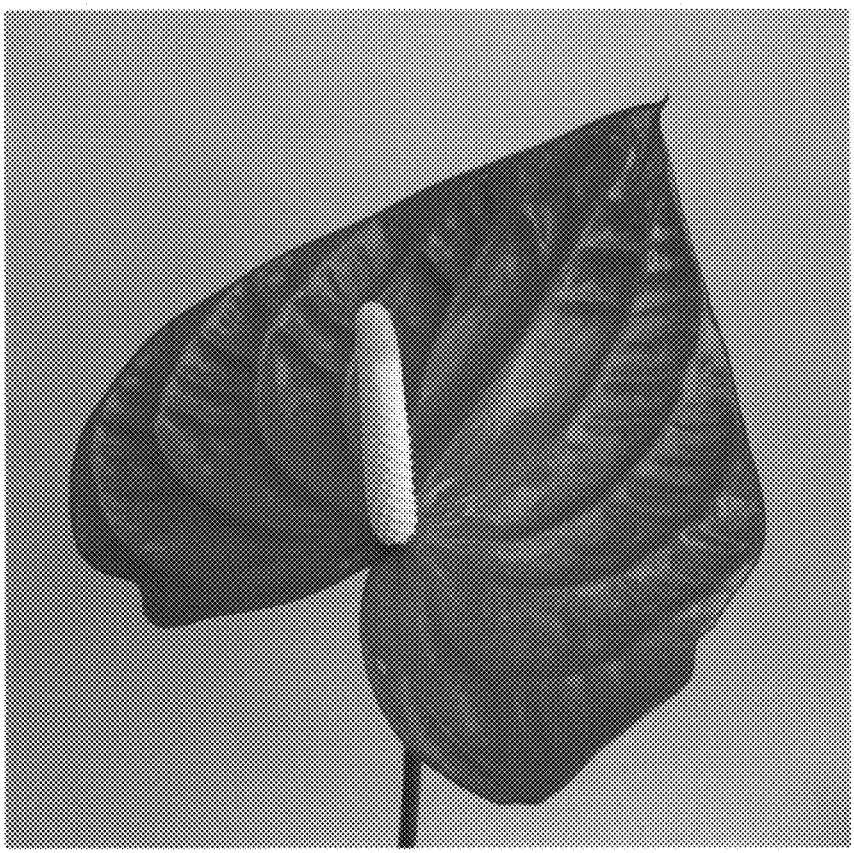
FIG. 2 shows a close-up of the mature spathe.
Figure 3:
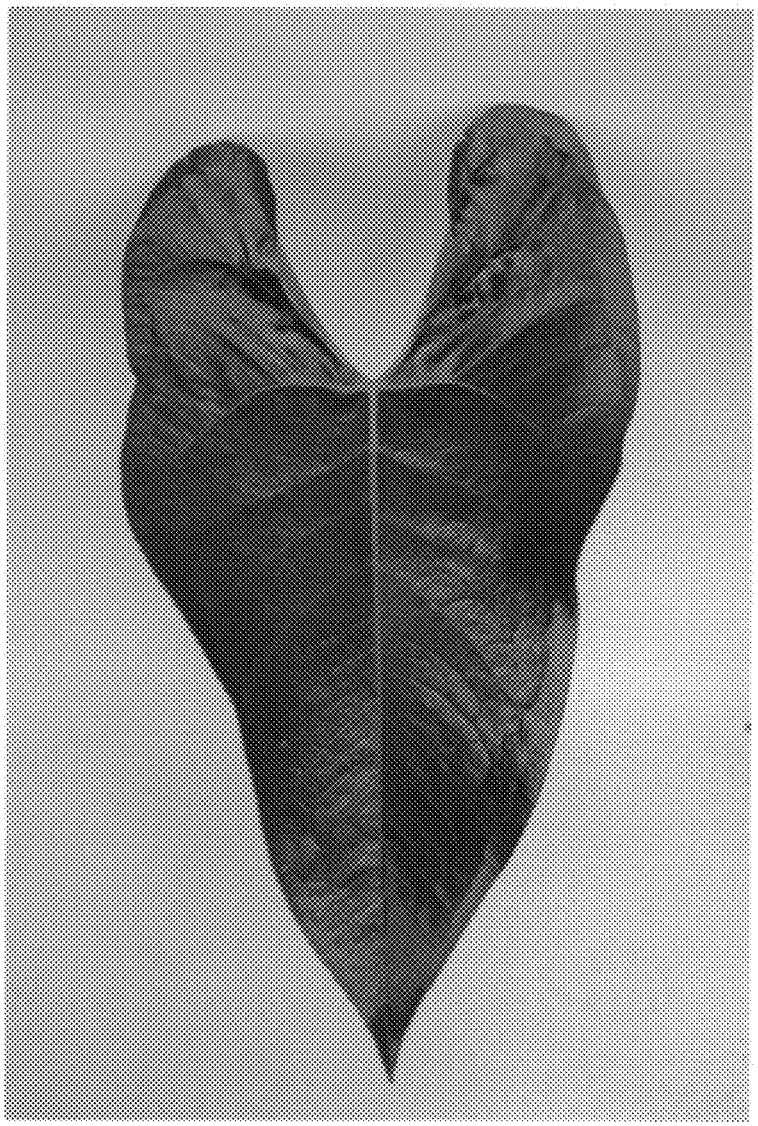
FIG. 3 shows a close-up of the upper leaf blade surface.

The following detailed description sets forth the distinctive characteristics of 'ANTHEUDAM'. The data which define these characteristics were collected from asexual reproductions carried out in Bleiswijk, The Netherlands. The plant history was taken on 52-week old plants which were planted from tissue culture in 17 centimeter (diameter) pots and grown in a glass greenhouse between 19° C. and 24° C. Observations were made in June 2017. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andreanum* L.

*Common name*.—*Anthurium*.

*Denomination*.—'ANTHEUDAM'.

Parentage:

*Female parent*.—*Anthurium* plant '10520-01' (unpatented).

*Male parent*.—*Anthurium* plant '9863-01' (unpatented).

Plant:

*Propagation*.—Tissue culture.

*Root description*.—Fleshy light yellow colored roots with light pink shade and small hairy lateral roots having yellow colored root tips.

*Time to produce a finished flowering plant*.—50 to 54 weeks after planting in a 17 cm (diameter) pot.

*Growth habit*.—Herbaceous perennial.

*Height* (*measured from soil, including inflorescence*).—45.0 cm to 50.0 cm.

*Width* (*measured from leaf tips*).—38.0 cm to 43.0 cm.

Leaves:

*Immature leaves*.—Length: 23.0 cm to 25.0 cm. Width: 11.0 cm to 13.0 cm. Color: Upper surface: RHS 146A. Lower surface: RHS 146B. Texture (both upper and lower surfaces): Shiny.

*Mature leaves*.—Length (fully expanded): 26.0 cm to 28.0 cm. Width: 13.0 cm to 15.0 cm. Shape: Elliptical cordate. Apex: Acuminate. Base: Cordate. Leaf blade angle with the petiole: Between 80 degrees and 100 degrees. Leaf margin: Entire. Color: Upper surface: RHS 147A. Lower surface: RHS 147B. Texture: Shiny, leathery and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 6.5 cm to 7.5 cm. Width of lobes of mature leaf blades: 5.5 cm to 6.5 cm. Distance from petiole/leaf junction to highest point on lobes of mature leaf: 5.0 cm to 6.0 cm.

*Petiole*.—Cross-section: Round. Diameter: 0.4 cm to 0.5 cm. Length: 23.0 cm to 25.0 cm for a mature leaf size. Color: Mature leaf: RHS 144A. Immature leaf: RHS 144A. Cataphyll color surrounding the petiole: Outside: RHS 144B/C. Inside: RHS 144D.

*Geniculum*.—Length: 2.5 cm to 3.0 cm. Width: 0.4 cm to 0.5 cm. Color: RHS 144B.

Inflorescence:

*Arrangement*.—Single.

*Flowering habit* (*length of flowering season*).—Continuous.

*Number of inflorescences per plant*.—5 to 7.

*Fragrance*.—Absent.

*Longevity of inflorescence on plant*.—Over a year.

Spathe:

*Buds*.—The spathe is tightly rolled around the spadix and extrudes from the peduncle sheath. After the spathe is fully open, the peduncle elongates some extra centimeters.

*Arrangement*.—Spathe angle with the peduncle is between 110 degrees and 120 degrees; the spathe stands on a wiry peduncle about 2.0 cm to 5.0 cm above the foliage.

*Shape*.—Cordate.

*Apex*.—Abruptly acuminate.

*Base*.—Cordate.

*Texture*.—Shiny and strongly blistered.

*Margin*.—Slightly undulated.

*Size*.—Length: 13.0 cm to 15.0 cm. Width: 12.0 cm to 13.0 cm.

*Lobes*.—Present.

*Arrangement*.—The spathe has two lobes extending past the peduncle. The lobes are non-touching. Length: 3.0 cm to 3.5 cm. Width: 5.5 cm to 6.5 cm.

*Color*.—Just fully open: Upper surface: RHS N45A/B. Lower surface: RHS N45C. This red color remains for a very long period, at least more than 30 weeks after opening.

Peduncle:

*Shape*.—Erect.

*Cross-section*.—Round.

*Length*.—38.0 cm to 43.0 cm.

*Diameter*.—0.4 cm to 0.6 cm.

*Color*.—RHS 144A.

Flowering time:

*General*.—One small, rooted, untreated tissue culture plant of 8.0 cm tall will flower, depending on season, after 50 to 52 weeks and 4 to 5 blossoms appear. More blossoms appear after some additional weeks so that a full flowering and commercial plant will have 6 to 7 red spathes. Smaller blossoms may occur on immature plants.

Spadix:

*Size*.—Length: 5.0 cm to 6.0 cm (depending on flower size). Width (at apex): 0.6 cm to 0.7 cm. Width (at base): 0.8 cm to 0.9 cm.

*Shape*.—Columnar.

*Angle from spadix tip to peduncle*.—170 degrees to 180 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 17A. Mature: RHS NN155A. Ages to: RHS 144B.

Flowers:

*Quantity per spadix*.—180 to 250.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: Many. Length: Less than 0.01 cm. Color: RHS 156D.

*Style*.—Not observed to date.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

COMPARISON WITH PARENTAL AND COMMERCIAL VARIETIES

'ANTHEUDAM' differs from the female parent plant '10520-01' (unpatented) in that 'ANTHEUDAM' has a wide spadix angle to spathe, whereas '10520-01' has a medium spadix angle to spathe. Additionally, 'ANTHEUDAM' has longer leaves than '10520-01'.

'ANTHEUDAM' differs from the male parent plant '9863-01' (unpatented) in that 'ANTHEUDAM' has cordate spathes and elliptical cordate leaves, whereas '9863-01' has oblong-cordate spathes and ovate-cordate leaves.

'ANTHEUDAM' differs from similar commercial variety 'ANTHDOTXI' (U.S. Plant Pat. No. 28,292) in that 'ANTHEUDAM' has a green cataphyll and an abruptly acuminate spathe apex, whereas 'ANTHDOTXI' has a red-brown cataphyll and a mucronate spathe apex. Additionally, 'ANTHEUDAM' has longer leaf lobes than 'ANTHDOTXI'.

'ANTHEUDAM' differs from similar commercial variety 'ANTHCITOK' (unpatented) in that 'ANTHEUDAM' has cordate, medium glossy spathes with an abruptly acuminate apex, a green cataphyll and a wide spadix angle to spathe, whereas 'ANTHCITOK' has orbicular cordate, strongly glossy spathes with a mucronate apex, a red-brown cataphyll and a medium spadix angle to spathe. Additionally, 'ANTHEUDAM' has longer leaf lobes than 'ANTHCITOK'.

I claim:

1. A new and distinct variety of *Anthurium* plant named 'ANTHEUDAM', substantially as illustrated and described herein.

* * * * *